United States Patent [19]

Butler

[11] Patent Number: 4,607,043

[45] Date of Patent: Aug. 19, 1986

[54] TETRAHYDRO-3,5-DIOXO-1H-PYRROLIZINE-7A(5H)-CARBOXYLIC ACIDS AND DERIVATIVES AS COGNITION ACTIVATORS

[75] Inventor: Donald E. Butler, Ann Arbor, Mich.

[73] Assignee: Warner-Lambert Company, Morris Plains, N.J.

[21] Appl. No.: 749,686

[22] Filed: Jun. 28, 1985

Related U.S. Application Data

[60] Division of Ser. No. 464,193, Feb. 9, 1983, Pat. No. 4,547,519, which is a continuation-in-part of Ser. No. 381,486, May 24, 1982, abandoned.

[51] Int. Cl.[4] .................. C07D 401/06; A61K 31/44
[52] U.S. Cl. ................................. 514/339; 514/363; 514/364; 514/381; 514/383; 514/359; 514/397; 514/406; 546/272; 548/251; 548/255; 548/268; 548/336; 548/374; 548/138; 548/143

[58] Field of Search ............... 546/272; 548/251, 255, 548/268, 336, 374, 138, 143; 514/339, 363, 364, 381, 383, 359, 397, 406

[56] References Cited

U.S. PATENT DOCUMENTS 4,145,347  3/1979  L'Italien et al. .................... 546/208
4,563,469  1/1986  Butler et al. ........................ 546/272

*Primary Examiner*—Jane T. Fan
*Attorney, Agent, or Firm*—Jerry F. Janssen

[57] ABSTRACT

Tetrahydro-3,5-dioxo-1H-pyrrolizine-7a(5H)-alkanoic acids, base addition salts, esters, and amides are useful as agents for the reversal of amnesia. Pharmaceutical compositions containing said compounds and methods for using said compositions for treating senility and reversal of amnesia are also taught.

6 Claims, No Drawings

TETRAHYDRO-3,5-DIOXO-1H-PYRROLIZINE-7A(5H)-CARBOXYLIC ACIDS AND DERIVATIVES AS COGNITION ACTIVATORS

This is a division of application Ser. No. 464,193 filed Feb. 9, 1983 now U.S. Pat. No. 4,547,519 issued Oct. 15, 1985, which is a continuation-in-part of U.S. patent application Ser. No. 381,486 of May 24, 1982, abandoned.

BACKGROUND OF THE INVENTION

The synthesis of tetrahydro-3,5-dioxo-1H-pyrrolizine-7a(5H)-propanoic acid ethyl ester is reported in Coll. Czech. Chem. Comm., 19, 298 (1954) (CA 49, 292c). The compound is utilized in the reference as a chemical intermediate.

SUMMARY OF THE INVENTION

The invention sought to be patented in its generic chemical compound aspect is a compound having the structural formula I

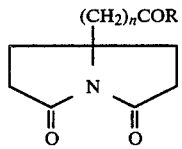

wherein n is zero to three and R is OH; O— as a salt with a pharmaceutically acceptable metal or amine cation; O-alkyl of from one to six carbon atoms or

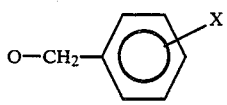

wherein X is hydrogen, alkyl of from one to six carbon atoms, alkoxy of from one to six carbon atoms, halo, or trifluoromethyl; with the proviso that when n is 2, R is not O-ethyl; or $NR_1R_2$ wherein $R_1$ is hydrogen, alkyl of from one to six carbon atoms or alkyl of from two to six carbon atoms substituted by amino, alkylamino, or dialkylamino in which alkyl contains one to six carbon atoms, hydroxy, or alkoxy of from one to six carbon atoms, mercapto, or alkylmercapto of from one to six carbon atoms, 5- or 6- membered cycloalkyl, 5- or 6- membered cycloalkyl substituted by alkyl of from one to four carbon atoms, phenyl or phenyl substituted by alkyl of from one to four carbon atoms, or a 5- or 6- membered heterocyclic group containing up to four heteroatoms consisting of nitrogen, oxygen, and sulfur which may be substituted by amino, alkylamino, dialkylamino, or alkyl of from one to four carbon atoms, and $R_2$ is hydrogen or alkyl of from one to six carbon atoms.

In a second generic aspect, the invention sought is a compound having the structural formula II, wherein

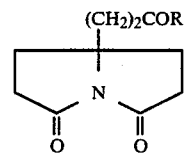

R is OH; O— as a salt with a pharmaceutically acceptable metal or amine cation;

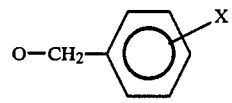

wherein X is hydrogen, alkyl of from one to six carbon atoms, alkoxy of from one to six carbon atoms, halo, or trifluoromethyl; or O-alkyl having one, three, four, five, or six carbon atoms; with the proviso that when n is 2, R is not O-ethyl; or $NR_1R_2$ wherein $R_2$ is hydrogen and $R_1$ is hydrogen, alkyl of from one to six carbon atoms, or alkyl of from two to six carbon atoms substituted by amino, alkylamino, or dialkylamino in which alkyl contains one to six carbon atoms, 2,6-dimethylphenyl, 4-amino-3-pyridinyl, 3-amino-4-pyridinyl, 4-pyridinyl, or 5-tetrazol-yl; or where $R_1R_2$ combine with N to form 2,6-dimethylpiperidine.

In a third generic concept, the invention sought is a compound having the structural formula III

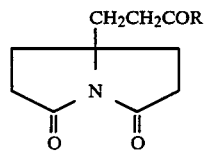

wherein R is OH; O— as a salt with a pharmaceutically acceptable metal or amine cation;

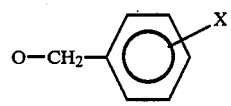

wherein X is hydrogen, alkyl of from one to six carbon atoms, alkoxy of from one to six carbon atoms, halo, or trifluoromethyl; or O-alkyl having one, three, four, five, or six carbon atoms.

The invention sought to be patented in a first specific chemical compound aspect is the compound having the name tetrahydro-3,5-dioxo-1H-pyrrolizine-7a-(5H)propanoic acid.

The invention sought to be patented in a second specific chemical compound aspect is the compound having the name tetrahydro-3,5-dioxo-1H-pyrrolizine-7a(5H)-propanoic acid benzyl ester.

The invention sought to be patented as further specific chemical compounds are the following:
tetrahydro-3,5-dioxo-1H-pyrrolizine-7a(5H)-carboxylic acid ethyl ester;
tetrahydro-3,5-dioxo-1H-pyrrolizine-7a(5H)-acetic acid;
tetrahydro-3,5-dioxo-1H-pyrrolizine-7a(5H)-butanoic acid;

tetrahydro-3,5-dioxo-1H-pyrrolizine-7a(5H)-butanoic acid benzyl ester;
tetrahydro-3,5-dioxo-1H-pyrrolizine-7a(5H)-propanoic acid amide;
tetrahydro-3,5-dioxo-1H-pyrrolizine-7a(5H)-propanoic acid N-N',N'-diisopropylaminoethyl amide;
tetrahydro-3,5-dioxo-1H-pyrrolizine-7a(5H)-propanoic acid N-5-tetrazol-yl amide; and
tetrahydro-3,5-dioxo-1H-pyrrolizine-7a(5H)-propanoic acid N-4-pyridinyl-amide.

The invention sought to be patented in its pharmaceutical composition aspect is a composition which comprises a compound having the structural formula IV

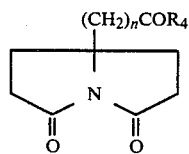

wherein $R_4$ is OH; O— as a salt with a pharmaceutically acceptable metal or amine cation; O-alkyl of from one to six carbon atoms; or

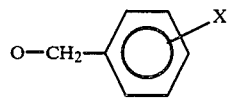

wherein X is hydrogen, alkyl of from one to six carbon atoms, alkoxy of from one to six carbon atoms, halo, or trifluoromethyl; or $NR_1R_2$ wherein $R_1$ is hydrogen, alkyl of from one to six carbon atoms or alkyl of from two to six carbon atoms substituted by amino, alkylamino, or dialkylamino in which alkyl contains one to six carbon atoms, hydroxy or alkoxy of from one to six carbon atoms, mercapto or alkylmercapto of from one to six carbon atoms, 5- or 6-membered cycloalkyl, 5- or 6-membered cycloalkyl substituted by alkyl of from one to four carbon atoms, phenyl or phenyl substituted by alkyl of from one to four carbon atoms or a 5- or 6-membered heterocyclic group containing up to four heteroatoms consisting of nitrogen, oxygen and sulfur which may be substituted by amino, alkylamino, dialkylamino, or alkyl of from one to four carbon atoms, and $R_1$ is hydrogen or alkyl of from one to six carbon atoms in combination with a pharmaceutically acceptable carrier.

The invention sought to be patented in a first specific pharmaceutical composition aspect is a composition which comprises tetrahydro-3,5-dioxo-1H-pyrrolizine-7a(5H)-propanoic acid, in combination with a pharmaceutically acceptable carrier.

The invention sought to be patented in a second specific pharmaceutical composition aspect is a composition which comprises tetrahydro-3,5-dioxo-1H-pyrrolizine-7a(5H)-propanoic acid ethyl ester in combination with a pharmaceutically acceptable carrier.

The invention sought to be patented in a third specific pharmaceutical composition aspect is a composition which comprises tetrahydro-3,5-dioxo-1H-pyrrolizine-7a(5H)-propanoic acid benzyl ester in combination with a pharmaceutically acceptable carrier.

The invention sought to be patented as further specific pharmaceutical compositions are the following compounds in combination with a pharmaceutically acceptable carrier:
tetahydro-3,5-dioxo-1H-pyrrolizine-7a(5H)-carboxylic acid ethyl ester;
tetrahydro-3,5-dioxo-1H-pyrrolizine-7a(5H)-acetic acid;
tetrahydro-3,5-dioxo-1H-pyrrolizine-7a(5H)-butanoic acid;
tetrahydro-3,5-dioxo-1H-pyrrolizine-7a(5H)-butanoic acid benzyl ester;
tetrahydro-3,5-dioxo-1H-pyrrolizine-7a(5H)-propanoic acid amide;
tetrahydro-3,5-dioxo-1H-pyrrolizine-7a(5H)-propanoic acid N-N',N'-diisopropylaminoethyl amide;
tetrahydro-3,5-dioxo-1H-pyrrolizine-7a(5H)-propanoic acid N-5-tetrazol-yl amide, and
tetrahydro-3,5-dioxo-1H-pyrrolizine-7a(5H)-propanoic acid N-4-pyridinyl amide.

The invention sought to be patented in its pharmaceutical method aspect is a method for treating senility or for reversing amnesia, which method comprises administering an effective amount of the above defined pharmaceutical composition to a mammal in need thereof.

DESCRIPTION OF THE PREFERRED EMBODIMENTS

The compounds of the invention when n is 2 in formula I, may be readily prepared from tetrahydro-3,5-dioxo-1H-pyrrolizine-7a-(5H)-propanoic acid ethyl ester by standard methods. The synthesis of this ethyl ester is reported in Coll. Czech. Chem. Comm., 19, 298 (1954) (CA. 49: 292c). Thus, the ethyl ester may be readily hydrolyzed by standard procedures to produce the acid having structural formula I wherein R is OH.

The acids having structural formula I wherein R is OH, tetrahydro-3,5-dioxo-1H-pyrrolizine-7a(5H)alkanoic acid, may also be prepared by reacting a compound of the formula V with a dehydrating agent such as an alkane acid anhydride, aryl acid anhydride, an alkane acid chloride or an aroyl chloride in the presence of an acid acceptor or by simply heating. The preferred process utilizes acetic anhydride, followed by hydrolysis with water in an inert solvent. Prior to the hydrolysis with water an intermediate compound is formed, which may be isolated. This intermediate has the structural formula VI, wherein R' is any convenient alkyl or aryl group. The starting material of structural formula V when n=2, may be prepared as described in U.S. Pat. No. 2,502,548.

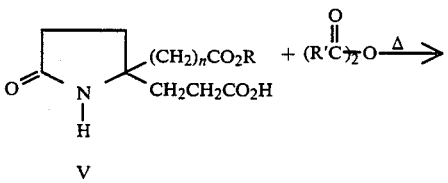

n = 0–3
R = H, or alkyl

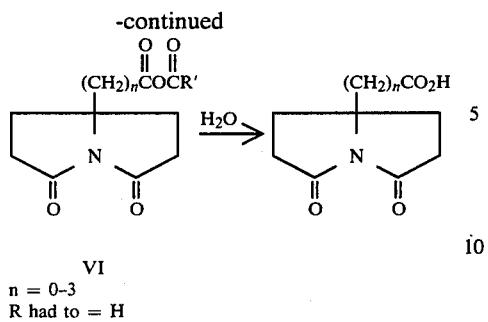

VI
n = 0–3
R had to = H

The acids may then be converted to additional compounds having structural formula I, i.e., salts, esters, and amides by standard procedures. For example, the salts may be prepared by treating the acid with an equivalent amount of a suitable base. The esters may be prepared by first converting the acid to an acid halide such as the acid chloride with, for example, thionyl chloride. The so produced acid chloride may then be treated with the desired alcohol, preferably in the presence of a suitable acid acceptor such as triethylamine or pyridine. The amides may also be prepared by first converting the acid to an acid halide such as the acid chloride. The so produced acid chloride may then be treated with the desired amine in an inert solvent, preferably methylene chloride, or in more polar aprotic solvents if solubility requires.

The treatment of Compound V with the dehydrating agent is conducted preferably in the absence of a solvent, although a halogenated hydrocarbon may be employed (dichloromethane, tetrachloroethane, or dichlorobenzene). The reactants are present in at least the ratio of one of the diacid to two of the dehydrating agents, although an excess of the dehydrating agent is preferred. This reaction may be carried out at a temperature range of 25° C. to 140° C. for periods of from 1 to 16 hours, preferably 100° C. to 140° C. for 12 to 16 hours.

The hydrolysis step is conveniently carried out in aq inert solvent in which the intermediate and water are soluble such as acetonitrile or tetrahydrofuran or simply by vigorous agitation of V with water. This hydrolysis is carried out at a temperature range of 25° C. to 85° C. for periods of from 1 to 24 hours, preferably 40° C. to 60° C. for six to eight hours.

The product may be isolated by filtration.

The compounds of the invention having structural formula I wherein R is OH form pharmaceutically acceptable salts with organic and inorganic bases. Examples of suitable inorganic bases for salt formation are sodium hydroxide, potassium hydroxide, sodium carbonate, calcium carbonate, potassium carbonate, sodium bicarbonate, and the like.

The term pharmaceutically acceptable amine cation contemplates the positively charged ammonium ion and analogous ions derived from organic nitrogenous bases strong enough to form such cations. Bases useful for the purpose of forming pharmacologically-acceptable nontoxic addition salts of such compounds containing free carboxyl groups form a class whose limits are readily understood by those skilled in the art. Merely for illustration they can be said to comprise in cationic form those of the formula:

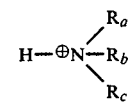

wherein $R_a$, $R_b$, and $R_c$, independently, are hydrogen alkyl of from about one to about six carbon atoms, cycloalkyl of from about three to about six carbon atoms, aryl of about six carbon atoms, aralkyl of from about 7 to about 11 carbon atoms, hydroxyalkyl of from about two to about four carbon atoms, or monoarylhydroxyalkyl of from about 8 to about 15 carbon atoms or, when taken together with the nitrogen atom to which they are attached, any two of $R_a$, $R_b$, and $R_c$ may form part of a 5 to 6-membered heterocyclic ring containing carbon, hydrogen, oxygen, or nitrogen, said heterocyclic rings and said aryl groups being unsubstituted or mono or dialkyl substituted said alkyl groups containing from about one to about six carbon atoms. Illustrative therefore of $R_a$, $R_b$, and $R_c$ groups comprising pharmacologically-acceptable cations derived from ammonia or a basic amine are ammonium, mono-, di-, and trimethylammonium, mono-, di-, and triethylammonium, mono-, di-, and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butylpiperidinium, 2-methylpiperidinium, 1-ethyl-2-methylpiperidinium, mono-, di- and triethanolammonium, ethyldiethanolammonium, n-butylmonoethanolammonium, tris(hydroxymethyl)-methylammonium, phenylmonoethanolammonium, and the like.

The term, pharmaceutically acceptable metal cation contemplates the positively charged ions derived from such metals as sodium, potassium, calcium, magnesium, aluminum, zinc, iron, and the like. The salts are prepared by contacting the free form of the compound with an equivalent amount of the desired base in the conventional manner. The free forms may be regenerated by treating the salt form with an acid. For example, dilute aqueous acid solutions may be utilized to regenerate the free form from a respective salt. Dilute aqueous hydrochloric acid is suitable for this purpose. The free forms differ from their respective salt forms somewhat in certain physical properties such as solubility in polar solvents, but the salts are otherwise equivalent to their respective free base forms for purposes of the invention.

The compounds of the invention can exist in unsolvated as well as solvated forms, including hydrated forms. In general, the solvated forms, with pharmaceutically acceptable solvents such as water, ethanol, and the like are equivalent to the unsolvated forms for purposes of the invention.

The alkyl groups contemplated by the invention unless otherwise stated, comprise both straight and branched carbon chains of from one to about six carbon atoms. Representative of such groups are methyl, ethyl, isopropyl, pentyl, 3-methylpentyl, and the like.

Cycloalkyl groups contemplated by the invention are those having five or six members such as cyclopentyl and cyclohexyl which may be optionally substituted by alkyl of one to four carbon atoms but especially methyl.

The heterocyclic groups contemplated by the invention are those having five or six ring members containing up to 4-heteroatoms consisting of N, O, and S, and especially those rings containing one to four nitrogen atoms and optionally an oxygen or sulfur atom when there are two or less nitrogen atoms. Illustrative of such groups are tetrazol-5-yl, 4-pyridinyl, 3-amino-4-pyridinyl, 4-amino-3-pyridinyl, 1,2,3-triazole-5-yl, 1,2,4-triazole-5-yl, 1,2-diazole-3-yl, 1,3-diazole-4-yl, 1,3-diazole-2-yl, 1,3,4-thiadiazole-2-yl, and 1,3,4-oxadiazole-2-yl. The above groups may also be substituted in the ring by alkyl of one to four carbon atoms, especially methyl.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. In the tablet, the active compound is mixed with a carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool, and thereby to solidify.

Liquid form preparations include solutions, suspensions, and emulsions. As an example, it may be mentioned water or water propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid from preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain in addition to the active material, flavorants, colorants, stabilizers, buffers, artificial and natural sweeteners, dispersants, thickeners, solubilizing agents, and the like. The liquid utilized for preparing the liquid from preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself, or it can be the appropriate number of any of these in packaged form.

The quantity of active compound in a unit dose of preparation may be varied or adjusted from 1 mg to 500 mg, preferably to 5 to 100 mg according to the particular application and the potency of the active ingredient. The compositions can, if desired, also contain other compatable therapeutic agents.

In therapeutic use as cognition activators, the mammalian dosage range for a 70 kg subject is from 1 to 1500 mg/kg of body weight per day or preferably 25 to 750 mg/kg of body weight per day. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The effectiveness of the aforementioned compounds was determined by the test designed to show the compound's ability to reverse amnesia produced by electroconvulsive shock. The test is fully described in U.S. Pat. No. 4,145,347, issued Mar. 20, 1979, and is herein incorporated by reference. The test compounds in the present instance were administered orally and the length of electroconvulsive shock was 1.0 second.

The following criteria are used in interpreting the percent of amnesia reversal scores: 40 percent or more (active=A), 25 to 39 percent (borderline=C), and 0 to 24 percent (inactive=N).

Table 1 below reports the percent of amnesia reversal of orally administered tetrahydro-3,5-dioxo-1H-pyrrolizine-7a(5H)-propanoic acid.

TABLE 1

| Dose mg/kg | 0.63 | 1.25 | 2.50 | 5.00 | 20.00 | 80.00 |
|---|---|---|---|---|---|---|
| % Reversal | 50 | 40 | 30 | 56 | 67 | 22 |
| Rating | A | A | C | A | A | N |

Table 2 below reports the percent of amnesia reversal of orally administered tetrahydro-3,5-dioxo-1H-pyrrolizine-7a(5H)-propanoic acid esters.

TABLE 2

| R Group | Dose in mg/kg % Reversal (Rating) | | |
|---|---|---|---|
| of Esters | 5.00 | 20.00 | 80.00 |
| $C_2H_5$ | 98(A) | 62(A) | 50(A) |
| $CH_2CH(CH_3)_2$ | 0(N) | 73(A) | 0(N) |
| $CH_2\phi$ | 40(A) | 40(A) | 60(A) |

Table 3 reports the percent amnesia reversal of other orally administered test compounds

TABLE 3

$(CH_2)_n COR$ on pyrrolizine-3,5-dione ring system

| Name | n | R | Dose mg/kg % Reversal (Rating) | | |
|---|---|---|---|---|---|
| | | | 1 | 10 | 100 |
| Tetrahydro-3,5-dioxo-1H—pyrrolizine-7a(5H)—carboxylic acid, ethyl ester | 0 | $OC_2H_5$ | 67(A) | 33(C) | 73(A) |
| Tetrahydro-3,5-dioxo-1H—pyrrolizine-7a(5H)—acetic acid | 1 | OH | 71(A) | 59(A) | 71(A) |
| Tetrahydro-3,5-dioxo-1H—pyrrolizine-7a(5H)—butanoic acid | 3 | OH | 57(A) | 64(A) | 57(A) |
| Tetrahydro-3,5-dioxo-1H—pyrrolizine-7a(5H)—butanoic acid, benzyl ester | 3 | $OCH_2C_6H_5$ | 47(A) | 76(A) | 46(A) |
| Tetrahydro-3,5-dioxo-1H—pyrrolizine-7a(5H)—propanoic acid amide | 2 | $NH_2$ | 71(A) | 64(A) | 50(A) |
| Tetrahydro-3,5-dioxo-1H—pyrrolizine-7a(5H)—propanoic acid, N—N', N'—diisopropylaminoethyl amide | 2 | $NR_1R_2$ | 31(C) | 31(C) | 57(A) |
| Tetrahydro-3,5-dioxo-1H—pyrrolizine-7a(5H)—propanoic acid, N—5-tetrazolyl amide | 2 | $NR_1R_2$ | 54(A) 35(A) | 64(A) 46(A) | 9(N) 46(A) |

CHEMICAL COMPOSITIONS

EXAMPLE A

Preparation of
Tetrahydro-3,5-dioxo-1H-pyrrolizine-7a(5H)-propanoic acid

A solution of 160 g of crude γ-carbomethoxyethyl-γ-nitropimelic acid dimethyl ester in 800 ml of methanol is hydrogenated at approximately 50 psi using 2 g of 20% Pd/C as catalyst. The resulting slurry is filtered to remove the catalyst and the filtrate is concentrated at reduced pressure to yield crude 5-oxo-2,2-pyrrolidinedipropanoic acid dimethyl ester and 5-oxo-2,2-pyrrolidinedipropanoic acid monomethyl ester. The crude esters are dissolved in 100 ml of methanol and 100 ml of water and are treated with 120 g of 50% sodium hydroxide solution. The reaction mixture is stirred and is heated to 100° C. with distillation of methanol. The solution is cooled, neutralized with 130 ml of concentrated hydrochloric acid, and concentrated at reduced pressure. The residue containing 5-oxo-2,2-pyrrolidinedipropanoic acid is heated at 98°–100° C. for 24 hours with 204 gm of acetic anhydride. The sodium chloride from the neutralization is removed by filtration after the acetic anhydride reaction. The filtrate is then concentrated at reduced pressure and 200 ml of toluene is added and concentration is repeated. The resulting oil is crude tetrahydro-3,5-dioxo-1H-pyrrolizine-7a(5H) propanoic acid anhydride with acetic acid. The oil is stirred vigorously with water or is reacted with water in acetonitrile and the tetrahydro-3,5-dioxo-1H-pyrrolizine-7a(5H)-propanoic acid is isolated by filtration. The tetrahydro-3,5-dioxo-1H-pyrrolizine-7a(5H)-propanoic acid may be recrystallized from tetrahydrofuran for purification giving product with a melting point of 179°–181° C.

EXAMPLE B

Preparation of
Tetrahydro-3,5-dioxo-1H-pyrrolizine-7a(5H)-propanoyl chloride

A suspension of 5 g (0.024 mole) of tetrahydro-3,5-dioxo-1H-pyrrolizine-7a(5H)-propanoic acid and one drop of pyridine in 150 ml of methylene chloride is treated with 2.85 g (0.024 mole) of thionyl chloride by dropwise addition. The mixture is stirred three hours. An additional 2.85 g (0.024 mole) of thionyl chloride is added and the mixture stirred one hour. The resulting solution is concentrated at reduced pressure to yield the product as a crystalline solid.

EXAMPLE C

Preparation of
Tetrahydro-3,5-dioxo-1H-pyrrolizine-7a(5H)-propanoic acid methyl ester A solution of 5.5 g (0.024 mole) of tetrahydro-3,5-dioxo-1H-pyrrolizine-7a(5H)-propanoyl chloride in 200 ml of dichloromethane is treated with 3.3 ml (0.024 mole) of triethylamine and 0.60 g (0.024 mole) of methanol with stirring. The mixture is stirred at room temperature for 30 minutes. The precipitate of triethylamine hydrochloride is removed by filtration. The filtrate is concentrated at reduced pressure and the residue purified by chromatography over silica gel using 20% anhydrous diethylether in dichloromethane as eluant. The fractions containing the product are concentrated at reduced pressure. The tetrahydro-3,5-dioxo-1H-pyrrolizine-7a(5H)-propanoic acid methyl ester crystallizes with a melting point of 110°–112° C.

EXAMPLE D

Preparation of
Tetrahydro-3,5-dioxo-1H-pyrrolizine-7a(5H)-propanoic acid benzyl ester A solution of 5.5 g (0.024 mole) of tetrahydro-3,5-dioxo-1H-pyrrolizine-7a(5H)-propanoyl chloride in 200 ml of dichloromethane is treated with 3.3 ml (0.024 mole) of triethylamine and 2.60 g (0.024 mole) of benzyl alcohol with stirring. The mixture is stirred at room temperature for 30 minutes. The precipitate of triethylamine hydrochloride is removed by filtration. The filtrate is concentrated at reduced pressure and the residue purified by chromatography over silica gel using 10% anhydrous diethylether in dichloromethane as eluant. The fractions containing the product are concentrated at reduced pressure. The tetrahydro-3,5-dioxo-1H-pyrrolizine-7a(5H)-propanoic acid benzyl ester crystallizes with a melting point of 80°–82° C.

EXAMPLE E

Preparation of Tetrahydro-3,5-dioxo-1H-pyrrolizine-7a(5H)-propanoic acid o-chlorobenzyl ester A solution of 5.5 g (0.024 mole) of tetrahydro-3,5-dioxo-1H-pyrrolizine-7a(5H)-propanoyl chloride in 200 ml of dichloromethane is treated with 3.3 ml (0.024 mole) of triethylamine and 3.41 g (0.024 mole) of o-chlorobenzyl alcohol with stirring. The mixture is stirred at room temperature for 30 minutes. The precipitate of triethylamine hydrochloride is removed by filtration. The filtrate is concentrated at reduced pressure and the residue purified by chromatography over silica gel using 10% anhydrous diethylether in dichloromethane as eluant. The fractions containing the product are concentrated at reduced pressure. The tetrahydro-3,5-dioxo-1H-pyrrolizine-7a(5H)-propanoic acid o-chlorobenzyl ester crystallizes with a melting point of 126°–128° C.

EXAMPLE F

Preparation of Tetrahydro-3,5-dioxo-1H-pyrrolizine-7a(5H)-propanoic acid p-chlorobenzyl ester A solution of 5.5 g (0.024 mole) of tetrahydro-3,5-dioxo-1H-pyrrolizine-7a(5H)-propanoyl chloride in 200 ml of dichloromethane is treated with 3.3 ml (0.024 mole) of triethylamine and 3.41 g (0.024 mole) of p-chlorobenzyl alcohol with stirring. The mixture is stirred at room temperature for 30 minutes. The precipitate of triethylamine hydrochloride is removed by filtration. The filtrate is concentrated at reduced pressure and the residue purified by chromatography over silica gel using 10% anhydrous diethylether in dichloromethane as eluant. The fractions containing the product are concentrated at reduced pressure. The tetrahydro-3,5-dioxo-1H-pyrrolizine-7a(5H)-propanoic acid p-chlorobenzyl ester crystallizes with a melting point of 141°–142° C.

EXAMPLE G

Preparation of Tetrahydro-3,5-dioxo-1H-pyrrolizine-7a(5H)-propanoic acid ethyl ester A solution of 5.5 g (0.024 mole) of tetrahydro-3,5-dioxo-1H-pyrrolizine-7a(5H)-propanoyl chloride in 200 ml of dichloromethane is treated with 3.3 ml (0.024 mole) of triethylamine and 1.1 g (0.024 mole) of ethanol with stirring. The mixture is stirred at room temperature for 30 minutes. The precipitate of triethylamine hydrochloride is removed by filtration. The filtrate is concentrated at reduced pressure and the residue purified by chromatography over silica gel using 10% anhydrous diethylether in dichloromethane as eluant. The fractions containing the product are concentrated at reduced pressure. The tetrahydro-3,5-dioxo-1H-pyrrolizine-7a(5H)-propanoic acid ethyl ester crystallizes with a melting point of 104°–105° C.

EXAMPLE H

Preparation of Tetrahydro-3,5-dioxo-1H-pyrrolizine-7a(5H)-propanoic acid 2-methylpropyl ester A solution of 5.5 g (0.024 mole) of tetrahydro-3,5-dioxo-1H-pyrrolizine-7a(5H)-propanoyl chloride in 200 ml of dichloromethane is treated with 3.3 ml (0.024 mole) of triethylamine and 1.78 g (0.024 mole) of 2-methylpropyl alcohol with stirring. The mixture is stirred at room temperature for 30 minutes. The precipitate of triethylamine hydrochloride is removed by filtration. The filtrate is concentrated at reduced pressure and the residue purified by chromatography over silica gel using 10% anhydrous diethylether in dichloromethane as eluant. The fractions containing the product are concentrated at reduced pressure. The tetrahydro-3,5-dioxo-1H-pyrrolizine-7a(5H)-propanoic acid 2-methylpropyl ester crystallizes with a melting point of 102°–104° C.

EXAMPLE I

Preparation of Tetrahydro-3,5-dioxo-1H-pyrrolizine-7a(5H)-butanoic acid, benzyl ester A suspension of 10 g (0.048 mole) of tetrahydro-3,5-dioxo-1H-pyrrolizine-7a(5H)-propanoic acid (synthesized as described in Example A) and one drop of pyridine in 150 ml of methylene chloride is treated with 5.7 g (0.048 mole) of thionyl chloride by dropwise addition. The mixture is stirred three hours. An additional 2.85 g (0.024 mole) of thionyl chloride is added and the mixture stirred one hour. The resulting solution is concentrated at reduced pressure to yield tetrahydro-3,5-dioxo-1H-pyrrolizine-7a(5H)-propanoyl chloride as a crystalline solid.

The solution of 9.6 g (0.04 mole) of the acid chloride in anhydrous diethyl ether (500 ml) is added to a solution of 6 g (0.14 mole) of diazomethane in anhydrous diethyl ether (500 ml). The mixture is stirred 16 hours at room temperature and is concentrated at reduced pressure. The resulting solid is chromatographed over silica and the product is eluted with 10% acetonitrile—90% chloroform. The concentration yields 4-[tetrahydro-3,5-dioxo-1H-pyrrolizine 7a(5H)]-1-diazo-2-butanone, mp 118°–120° C.

A solution of 6.4 g (0.027 mole) of the 1-diazo-2-butanone in benzyl alcohol (50 ml) is added with stirring to a suspension of 1 g of Ag$_2$O in benzyl alcohol (100 ml) at 80° C. The suspension is stirred at 80° C. until the N$_2$ evolution has ended. The mixture is stirred 16 hours at room temperature and filtered through filter aid. After concentration at reduced pressure (0.9 mm), the residue is chromatographed over silica gel eluting with 10% anhydrous diethyl ether in methylene chloride. The tetrahydro-3, 5-dioxo-1H-pyrrolizine-7a(5H)-butanoic acid, benzyl ester is isolated as a crystalline solid with melting point of 102°–105° C. by concentration of the eluate at reduced pressure.

EXAMPLE J

Synthesis of Tetrahydro-3,5-dioxo-1H-pyrrolizine-7a(5H)-butanoic acid

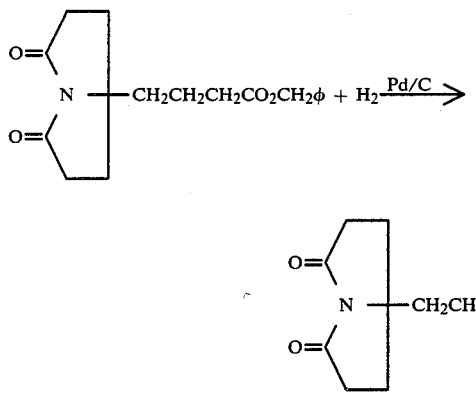

A solution of 1.0 g (0.0032 mole) tetrahydro-3,5-dioxo-1H-pyrrolizine-7a(5H)-butanoic acid, benzyl ester, prepared in Example I in tetrahydrofuran (30 ml) is treated with hydrogen in the presence of 0.1 g of a 20% Pd/C catalyst. The resulting solution is filtered to remove the catalyst and the product crystallizes upon concentration. Recrystallization from acetonitrile yields tetrahydro-3,5-dioxo-1H-pyrrolizine-7a(5H)-butanoic acid with a melting point of 178°-180° C.

EXAMPLE K

Synthesis of Tetrahydro-3,5-dioxo-1H-pyrrolizine-7a(5H)carboxylic acid, ethyl ester A solution of 172.18 g (2 mole) methyl acrylate and 10 g of Triton B in t-butanol is heated to 60° C. and with stirring 133.10 g (1.0 mole) of ethyl α-nitroacetate [CAS number 614-18-6] is added dropwise. When the addition is complete, another 5 g of Triton B (benzyltrimethylammonium hydroxide, available from Aldrich Chemicals, J. T. Baker Chemical Co., etc) is added and the mixture is maintained at 60° C. for 16 hours. The mixture is cooled and poured into a solution of 20 ml of concentrated hydrochloric acid in water (1 l). The solution is extracted with dichloromethane (2×1 l), dried over anhydrous magnesium sulfate, filtered, concentrated, and distilled to yield dimethyl-γ-carboethoxy-γ-nitro pimelate, bp 140°-145° C. at 0.6 mm.

A solution of 240.5 g (0.79 mole) dimethyl-γ-carboethoxy-γnitro pimelate in methanol (3.78 l) is treated with hydrogen in the presence of 10 g of 20% Pd/C. The mixture is filtered and concentrated to yield a crude mixture of 5-carboethoxy-5-carbomethoxyethyl-2-pyrrolidinone and 5-carboethoxy-5-carboxyethyl-2-pyrrolidinone as an oil. The oil dissolved in methanol (500 ml) is treated with a solution of sodium hydroxide (56.6 g, 1.4 mole) in water (557 ml). The mixture is stirred and methanol is distilled until the temperature of the solution reaches 99° C. The mixture is cooled to 10° C. and treated with 116.7 ml (1.42 mol) of concentrated hydrochloric acid to yield an aqueous solution of 5-carboethoxy-5-carboxyethyl-2-pyrrolidinone. The water is removed by concentration at reduced pressure and the resulting oil is added to 1 kg of acetic anhydride with stirring. The mixture is heated at 100° C. for 16 hours and filtered through filter aid. After concentration at reduced pressure, the oil is distilled, bp 135°-150° C. at 0.5 mm. Chromatography over silica gel followed by elution with 20% anhydrous diethyl ether in methylene chloride yields after concentration of the eluate, tetrahydro-3,5-dioxo-1H-pyrrolizine-7a(5H)-carboxylic acid, ethyl ester, mp 77°-82° C.

EXAMPLE L

Synthesis of Tetrahydro-3,5-dioxo-1H-pyrrolizine-7a(5H)-acetic acid

A suspension of 116 g (0.97 mole) β-nitropropanoic acid (CAS number 504-88-1) in chloroform (1 l) is stirred and treated with 127.5 g (1.07 mole) thionyl chloride. A rapid evolution of gas takes place and the mixture is stirred one hour at room temperature. Ethanol (50 g, 1.07 mole) is added dropwise followed by rapid gas evolution. The mixture is stirred 72 hours, concentrated and distilled to yield ethyl β-nitropropanoate, bp 95°-105° C. at 15 mm. A solution of 182 g (1.84 mole) ethyl acrylate [CAS number 140-88-5] in t-butanol (150 ml) and 10 ml of Triton B is treated at 40° C. with 135.5 g (0.92 mole) of ethyl β-nitropropanoate. Additional portions of Triton B (2 ml×3) and ethyl acrylate (25 g×3) are added over a five-hour period. The mixture is cooled and poured into a solution of 100 ml of concentrated hydrochloric acid in water (1 l). The diethyl-γ-nitro-γ-carboethoxymethylpimelate is extracted using dichloromethane (4×500 ml). The combined extracts are dried over anhydrous magnesium sulfate, filtered, and concentrated to yield an oil. The oil (160 g) is dissolved in ethanol (1.5 l) and treated with hydrogen in the presence of 7 g 20% Pd/C. The mixture is filtered through filter aid and concentrated to yield a mixture of 5-carboethoxyethyl-5-carboethoxymethyl-2-pyrrolidinone (major product), 5-carboethoxymethyl-5-carboxyethyl-2-pyrrolidinone, and 5-carboethoxyethyl-5-carboxymethyl-2-pyrrolidinone as an oil. The oil dissolved in 1 l of 50% ethanol is titrated with a solution of 50% sodium hydroxide with stirring at reflux accompanied by removal of ethanol. The hydrolyzed mixture is neutralized with concentrated hydrochloric acid to yield 5-carboxyethyl-5-carboxymethyl-2-pyrrolidinone in water. The water is removed at reduced pressure and the resulting solid is added to acetic anhydride (1 kg) with stirring. The mixture is heated at 100° C. for 16 hours. The mixture is filtered through filter aid and concentrated at reduced pressure to yield tetrahydro-3,5-dioxo-1H-pyrrolizine-7a(5H) acetic acid anhydride with acetic acid as an oil. The oil is dissolved in a mimimum amount of acetonitrile, an equivalent amount of water is added, and the mixture is stirred 16 hours. The mixture is concentrated at reduced pressure to yield a solid. The solid is recrystallized from acetonitrile to yield tetrahydro-3,5-dioxo-1H-pyrrolizine-7a(5H)-acetic acid with a melting point of 177°-180° C.

EXAMPLE M

Synthesis of Tetrahydro-3,5-dioxo-1H-pyrrolizine-7a-(5H)-propanoic acid amide Anhydrous ammonia is bubbled through a solution of 5.0 g of tetrahydro-3,5-dioxo-1H pyrrolizine-7a(5H)-propanoyl chloride in 100 ml methylene chloride at room temperature. The immediately crystalline by-product, NH₄Cl, is removed by filtration. Upon standing, the desired product crystallizes as a white precipitate. The white precipitate formed is collected and recrystallized from methanol, mp 173°–175° C.

EXAMPLE N

Preparation of tetrahydro-3,5-dioxo-1H-pyrrolizine-7a(5H)-propanoic acid N-5-tetrazol-yl amide To a solution of 2.7 g of 5-amino tetrazole in 100 ml acetone at room temperature is added 6.0 g of tetrahydro-3,5-dioxo-1H pyrrolizine-7a(5H)-propanoyl chloride in 325 ml of acetone at a fast dropping rate and 3.6 g of triethylamine is then added. The white precipitate which forms immediately is collected and is washed with boiling acetone followed by boiling toluene, leaving the product as a white solid, which melts with decomposition at 191°–195° C.

EXAMPLE O

Preparation of tetrahydro-3,5-dioxo-1H-pyrrolizine-7a(5H)-propanoic N-N′N′-diisopropylamino ethyl amide mono-hydrochloride A solution of N-[2[bis(1-methylethyl)amino]ethylamine] (6.5 g) in 50 ml methylene chloride is added to a solution of (5.0 g) of tetrahydro-3,5-dioxo-1H pyrrolizine-7a(5H)-propanoyl chloride in 100 ml methylene chloride at room temperature. After stirring 16 hours at reflux, the solvent is removed in vacuo, the residue is dissolved in acetonitrile, treated with charcoal, and filtered through celite. Upon cooling, the crystalline product is isolated by filtration with a melting point of 184°–186° C.

EXAMPLE P

Preparation of tetrahydro-3,5-dioxo-1H-pyrrolizine-7a(5H)-propanoic acid N-4-pyridinyl amide A suspension of 21.1 g of tetrahydro-3,5-dioxo-1H-pyrrolizine-7a(5H)-propanoic acid, 21.7 g of dicyclohexylcarbodiimide, and 100 mg of 4-dimethylaminopyridine (catalyst) in 100 ml of methylene chloride are treated with 9.4 g of 4-aminopyridine. The mixture is stirred for 16 hours and the by-product, N,N¹-dicyclohexylurea, is removed by filtration. The product is purified by chromatography over silica gel using 40% 2-propanol-methylene chloride for elution. After recrystallization from water, the product is isolated as a white solid with a melting point of 285°–287° C.

The invention is further illustrated by the following examples of tablets containing 1.0, 2.5, 25, 50 mg; capsules containing 1.0, 2.5, 25, 50 mg respectively of active ingredient, an example of a parenteral formulation, an example of a rectal suppository formulation, an example of a suspension formulation, and an example of a syrup for reconstitution formulation for oral administration.

PHARMACEUTICAL COMPOSITIONS

EXAMPLE 1

| Ingredient | Quantity |
|---|---|
| Tetrahydro-3,5-dioxo-1H—pyrrolizine-7a(5H)—propanoic acid | 150 g |
| Lactose | 1124 g |
| Corn Starch | 39 g |
| Hydroxypropyl cellulose | 30 g |
| Magnesium stearate | 7 g |
| Ethanol-water 50:50 | qs |

The tetrahydro-3,5-dioxo-1H-pyrrolizine-7a(5H)-propanoic acid, lactose, and hydroxypropyl cellulose are blended and granulated with 50:50 ethanol water. The wet granulation is screened, dried, and rescreened. The resulting dried granulation is blended with magnesium stearate and the corn starch, and the mixture is compressed into 225 mg tablets using an 11/32 inch standard concave punch. Yield equals approximately 6000 tablets each containing 25.0 mg of tetrahydro-3,5-dioxo-1H-pyrrolizine-7a(5H)-propanoic acid.

EXAMPLE 2

| Ingredient | Quantity |
|---|---|
| Tetrahydro-3,5-dioxo-1H—pyrrolizine-7a(5H)—propanoic acid | 15 g |
| Lactose | 1249 g |
| Corn Starch | 39 g |
| Hydroxypropyl cellulose | 30 g |
| Magnesium stearate | 7 g |
| Ethanol-water 50:50 | qs |

The tetrahydro-3,5-dioxo-1H-pyrrolizine-7a(5H)-propanoic acid, lactose, and hydroxypropyl cellulose are blended and granulated with 50:50 ethanol water. The wet granulation is screened, dried, and rescreened. The resulting dried granulation is blended with magnesium stearate and the corn starch, and the mixture is compressed into 225 mg tablets using an 11/32 inch standard concave punch. Yield equals approximately 6000 tablets each containing 2.5 mg of tetrahydro-3,5-dioxo-1H-pyrrolizine-7a(5H)-propanoic acid.

EXAMPLE 3

| Ingredient | Quantity |
|---|---|
| Tetrahydro-3,5-dioxo-1H—pyrrolizine-7a(5H)—propanoic acid | 6 g |
| Lactose | 1268 g |
| Corn Starch | 39 g |
| Hydroxypropyl cellulose | 30 g |
| Magnesium stearate | 7 g |
| Ethanol-water 50:50 | qs |

The tetrahydro-3,5-dioxo-1H-pyrrolizine-7a(5H)-propanoic acid, lactose, and hydroxypropyl cellulose are blended and granulated with 50:50 ethanol water. The wet granulation is screened, dried, and rescreened. The resulting dried granulation is blended with magnesium stearate and the corn starch, and the mixture is compressed into 225 mg tablets using an 11/32 inch standard concave punch. Yield equals approximately 6000 tablets each containing 1.0 mg of tetrahydro-3,5-dioxo-1H-pyrrolizine-7a(5H)-propanoic acid.

EXAMPLE 4

| Ingredient | Quantity |
|---|---|
| Tetrahydro-3,5-dioxo-1H—pyrrolizine-7a(5H)—propanoic acid | 300 g |

| Ingredient | Quantity |
| --- | --- |
| Lactose | 974 g |
| Corn Starch | 39 g |
| Hydroxypropyl cellulose | 30 g |
| Magnesium stearate | 7 g |
| Ethanol-water 50:50 | qs |

The tetrahydro-3,5-dioxo-1H-pyrrolizine-7a(5H)-propanoic acid, lactose, and hydroxypropyl cellulose are blended and granulated with 50:50 ethanol water. The wet granulation is screened, dried, and rescreened. The resulting dried granulation is blended with magnesium stearate and the corn starch, and the mixture is compressed into 225 mg tablets using an 11/32 inch standard concave punch. Yield equals approximately 6000 tablets each containing 50.0 mg of tetrahydro-3,5-dioxo-1H-pyrrolizine-7a(5H)-propanoic acid.

EXAMPLE 5

| Ingredient | Quantity |
| --- | --- |
| Tetrahydro-3,5-dioxo-1H—pyrrolizine-7a(5H)—propanoic acid | 250 g |
| Lactose | 1723 g |
| Magnesium stearate | 27 g |

The mixture is blended and filled into No. 4 hard gelatin capsules, filling each capsule with 200 mg of the powder mixture. Yield equals approximately 10,000 capsules each containing 25.0 mg of tetrahydro-3,5-dioxo-1H-pyrrolizine-7a(5H)-propanoic acid.

EXAMPLE 6

| Ingredient | Quantity |
| --- | --- |
| Tetrahydro-3,5-dioxo-1H—pyrrolizine-7a(5H)—propanoic acid | 25 g |
| Lactose | 1948 g |
| Magnesium stearate | 27 g |

The mixture is blended and filled into No. 4 hard gelatin capsules, filling each capsule with 200 mg of the powder mixture. Yield equals approximately 10,000 capsules each containing 2.5 mg of tetrahydro-3,5-dioxo-1H-pyrrolizine-7a(5H)-propanoic acid.

EXAMPLE 7

| Ingredient | Quantity |
| --- | --- |
| Tetrahydro-3,5-dioxo-1H—pyrrolizine-7a(5H)—propanoic acid | 10 g |
| Lactose | 1963 g |
| Magnesium stearate | 27 g |

The mixture is blended and filled into No. 4 hard gelatin capsules, filling each capsule with 200 mg of the powder mixture. Yield equals approximately 10,000 capsules each containing 1.0 mg of tetrahydro-3,5-dioxo-1H-pyrrolizine-7a(5H)-propanoic acid.

EXAMPLE 8

| Ingredient | Quantity |
| --- | --- |
| Tetrahydro-3,5-dioxo-1H—pyrrolizine-7a(5H)—propanoic acid | 500 g |
| Lactose | 1473 g |
| Magnesium stearate | 27 g |

The mixture is blended and filled into No. 4 hard gelatin capsules, filling each capsule with 200 mg of the powder mixture. Yield equals approximately 10,000 capsules each containing 50.0 mg of tetrahydro-3,5-dioxo-1H-pyrrolizine-7a(5H)-propanoic acid.

The invention is further illustrated by the following example of a 2 g rectal suppository. The suppository can contain a range of from 30 mg to 500 mg of active ingredient.

EXAMPLE 9

| Ingredient | Quantity |
| --- | --- |
| Tetrahydro-3,5-dioxo-1H—pyrrolizine-7a(5H)—propanoic acid | 30 mg |
| Witepsol H35 | 1.97 g |

The Witepsol H35 is melted by heating to 38° C., the tetrahydro-3,5-dioxo-1H-pyrrolizine-7a(5H)-propanoic acid is added and mixed until thoroughly dispersed, and placed in a mold at 33°–34° C.

The invention is further illustrated by the following example of a suspension formulation. The suspension can contain a range of active ingredient from 50 mg/5 ml to 1 g/5 ml.

EXAMPLE 10

| Ingredient | Quantity |
| --- | --- |
| Tetrahydro-3,5-dioxo-1H—pyrrolizine-7a(5H)—propanoic acid | 10 g |
| Saccharin Sodium | 0.5 g |
| Trihydroxystearin | 0.75 g |
| Propylparaben | 0.1 g |
| Imitation Cherry Flavor | 2 ml |
| Neobee M-5 q.s. ad | 100 ml |

Propylparaben is dissolved in a portion of the Neobee M-5, the trihydroxystearin is added and the mixture is homogenized for 30 minutes while maintaining the temperature between 50°–60° C. The mixture is cooled and the tetrahydro-3,5-dioxo-1H-pyrrolizine-7a(5H)-propanoic acid, saccharin sodium and imitation cherry flavor are added. The volume is made up with Neobee M-5.

The invention is further illustrated by the following example of a Syrup for Reconstitution. The syrup can contain between 50 mg/5 ml, and 500 mg/5 ml.

EXAMPLE 11

| Ingredient | Quantity |
| --- | --- |
| Tetrahydro-3,5-dioxo-1H—pyrrolizine-7a(5H)—propanoic acid | 5 g |
| Sugar granulated, Bottlers grade | 60 g |
| Artificial Peppermint Flavor, water Soluble | 0.4 g |
| Water q.s. ad | 100 ml |

The tetrahydro-3,5-dioxo-1H-pyrrolizine-7a (5H)-propanoic acid, granulated sugar, and artificial peppermint flavor are dry blended. The blend is filled into a bottle with a 100 ml calibration mark. At time of dispensing, make up to volume with water and shake until all solids are dissolved. The syrup contains 250 mg active per 5 ml. The mixture is refrigerated and used within 7 days.

The invention is further illustrated by the following example of a 2 g rectal suppository. The suppository can contain a range of from 30 mg to 500 mg of active ingredient.

EXAMPLE 12

| Ingredient | Quantity |
| --- | --- |
| Tetrahydro-3,5-dioxo-1H—pyrrolizine-7a(5H)—propanoic acid ethyl ester | 30 mg |
| Witepsol H35 | 1.97 g |

The Witepsol H35 is melted by heating to 38° C., the tetrahydro-3,5-dioxo-1H-pyrrolizine-7a(5H)-propanoic acid ethyl ester is added and mixed until thoroughly dispersed, and placed in a mold at 33°–34° C.

The invention is further illustrated by the following example of a suspension formulation. The suspension can contain a range of active ingredient from 50 mg/5 ml to 1 g/5 ml.

EXAMPLE 13

| Ingredient | Quantity |
| --- | --- |
| Tetrahydro-3,5-dioxo-1H—pyrrolizine-7a(5H)—propanoic acid ethyl ester | 10 g |
| Saccharin Sodium | 0.5 g |
| Trihydroxystearin | 0.75 g |
| Propylparaben | 0.1 g |
| Imitation Cherry Flavor | 2 ml |
| Neobee M-5 q.s. ad | 100 ml |

Propylparaben is dissolved in a portion of the Neobee M-5, the trihydroxystearin is added, and the mixture is homogenized for 30 minutes while maintaining the temperature between 50°–60° C. The mixture is cooled and the tetrahydro-3,5-dioxo-1H-pyrrrolizine-7a(5H)-propanoic acid ethyl ester, saccharin sodium, and imitation cherry flavor are added. The volume is made up with Neobee M-5.

The invention is further illustrated by the following example of a Syrup for Reconstitution. The syrup can contain between 50 mg/5 ml, and 500 mg/5 ml.

EXAMPLE 14

| Ingredient | Quantity |
| --- | --- |
| Tetrahydro-3,5-dioxo-1H—pyrrolizine-7a(5H)—propanoic acid ethyl ester | 10 g |
| Sugar granulated, Bottlers grade | 60 g |
| Artificial Peppermint Flavor, water Soluble | 0.4 g |
| Water q.s. ad | 100 ml |

The tetrahydro-3,5-dioxo-1H-pyrrolizine-7a(5H)-propanoic acid ethyl ester, granulated sugar, and artificial peppermint flavor are dry blended. The blend is filled into a bottle with a 100 ml calibration mark. At time of dispensing, make up to volume with water and shake until all solids are dissolved. The syrup contains 500 mg active per 5 ml. The mixture is refrigerated and used within 7 days.

The invention is further illustrated by the following example of a 2 g rectal suppository. The suppository can contain a range of from 30 mg to 500 mg of active ingredient.

EXAMPLE 15

| Ingredient | Quantity |
| --- | --- |
| Tetrahydro-3,5-dioxo-1H—pyrrolizine-7a(5H)—propanoic acid benzyl ester | 30 mg |
| Witepsol H35 | 1.97 g |

The Witepsol H35 is melted by heating to 38° C., the tetrahydro-3,5-dioxo-1H-pyrrolizine-7a(5H)-propanoic acid benzyl ester is added and mixed until thoroughly dispersed, and placed in a mold at 33°–34° C.

The invention is further illustrated by the following example of a suspension formulation. The suspension can contain a range of active ingredient from 50 mg/5 ml to 1 g/5 ml.

EXAMPLE 16

| Ingredient | Quantity |
| --- | --- |
| Tetrahydro-3,5-dioxo-1H—pyrrolizine-7a(5H)—propanoic acid benzyl ester | 10 g |
| Saccharin Sodium | 0.5 g |
| Trihydroxystearin | 0.75 g |
| Propylparaben | 0.1 g |
| Imitation Cherry Flavor | 2 ml |
| Neobee M-5 q.s. ad | 100 ml |

Propylparaben is dissolved in a portion of the Neobee M-5, the trihydroxystearin is added, and the mixture is homogenized for 30 minutes while maintaining the temperature between 50°–60° C. The mixture is cooled and the tetrahydro-3,5-dioxo-1H-pyrrrolizine-7a(5H)-propanoic acid benzyl ester, saccharin sodium, and imitation cherry flavor are added. The volume is made up with Neobee M-5.

The invention is further illustrated by the following example of a Syrup for Reconstitution. The syrup can contain between 50 mg/5 ml and 500 mg/5 ml.

EXAMPLE 17

| Ingredient | Quantity |
| --- | --- |
| Tetrahydro-3,5-dioxo-1H—pyrrolizine-7a(5H)—propanoic acid benzyl ester | 5 g |
| Sugar granulated, Bottlers grade | 60 g |
| Artificial Peppermint Flavor, water Soluble | 0.4 g |
| Water q.s. ad | 100 ml |

The tetrahydro-3,5-dioxo-1H-pyrrolizine-7a(5H)-propanoic acid benzyl ester, granulated sugar, and artificial peppermint flavor are dry blended. The blend is filled into a bottle with a 100 ml calibration mark. At time of dispensing, make up to volume with water and shake until all solids are dissolved. The syrup contains 250 mg active per 5 ml. The mixture is refrigerated and used within 7 days.

The invention is further illustrated by the following example of a 2 g rectal suppository. The suppository can contain a range of from 30 mg to 500 mg of active ingredient.

EXAMPLE 18

| Ingredient | Quantity |
|---|---|
| Tetrahydro-3,5-dioxo-1H—pyrrolizine-7a(5H)—propanoic acid o-chlorobenzyl ester | 30 mg |
| Witepsol H35 | 1.97 g |

The Witepsol H35 is melted by heating to 38° C., the tetrahydro-3,5-dioxo-1H-pyrrolizine-7a(5H)-propanoic acid o-chlorobenzyl ester is added and mixed until thoroughly dispersed, and placed in a mold at 33°-34° C.

The invention is further illustrated by the following example of a suspension formulation. The suspension can contain a range of active ingredient from 50 mg/5 ml to 1 g/5 ml.

EXAMPLE 19

| Ingredient | Quantity |
|---|---|
| Tetrahydro-3,5-dioxo-1H—pyrrolizine-7a(5H)—propanoic acid o-chlorobenzyl ester | 10 g |
| Saccharin Sodium | 0.5 g |
| Trihydroxystearin | 0.75 g |
| Propylparaben | 0.1 g |
| Imitation Cherry Flavor | 2 ml |
| Neobee M-5 q.s. ad | 100 ml |

Propylparaben is dissolved in a portion of the Neobee M-5, the trihydroxystearin is added, and the mixture is homogenized for 30 minutes while maintaining the temperature between 50°-60° C. The mixture is cooled and the tetrahydro-3,5-dioxo-1H-pyrrrolizine-7a(5H)-propanoic acid o-chlorobenzyl ester, saccharin sodium, and imitation cherry flavor are added. The volume is made up with Neobee M-5.

The invention is further illustrated by the following example of a Syrup for Reconstitution. The syrup can contain between 50 mg/5 ml, and 500 mg/5 ml.

EXAMPLE 20

| Ingredient | Quantity |
|---|---|
| Tetrahydro-3,5-dioxo-1H—pyrrolizine-7a(5H)—propanoic acid o-chlorobenzyl ester | 1 g |
| Sugar granulated, Bottlers grade | 60 g |
| Artificial Peppermint Flavor, water Soluble | 0.4 g |
| Water q.s. ad | 100 ml |

The tetrahydro-3,5-dioxo-1H-pyrrolizine-7a(5H)-propanoic acid o-chlorobenzyl ester, granulated sugar, and artificial peppermint flavor are dry blended. The blend is filled into a bottle with a 100 ml calibration mark. At time of dispensing, make up to volume with water and shake until all solids are dissolved. The syrup contains 50 mg active per 5 ml. The mixture is refrigerated and used within 7 days.

The invention is further illustrated by the following example of a 2 g rectal suppository. The suppository can contain a range of from 30 mg to 500 mg of active ingredient.

EXAMPLE 21

| Ingredient | Quantity |
|---|---|
| Tetrahydro-3,5-dioxo-1H—pyrrolizine-7a(5H)—propanoic acid p-chlorobenzyl ester | 30 mg |
| Witepsol H35 | 1.97 g |

The Witepsol H35 is melted by heating to 38° C., the tetrahydro-3,5-dioxo-1H-pyrrolizine-7a(5H)-propanoic acid p-chlorobenzyl ester is added and mixed until thoroughly dispersed, and placed in a mold at 33°-34° C.

The invention is further illustrated by the following example of a suspension formulation. The suspension can contain a range of active ingredient from 50 mg/5 ml to 1 g/5 ml.

EXAMPLE 22

| Ingredient | Quantity |
|---|---|
| Tetrahydro-3,5-dioxo-1H—pyrrolizine-7a(5H)—propanoic acid p-chlorobenzyl ester | 10 g |
| Saccharin Sodium | 0.5 g |
| Trihydroxystearin | 0.75 g |
| Propylparaben | 0.1 g |
| Imitation Cherry Flavor | 2 ml |
| Neobee M-5 q.s. ad | 100 ml |

Propylparaben is dissolved in a portion of the Neobee M-5, the trihydroxystearin is added, and the mixture is homogenized for 30 minutes while maintaining the temperature between 50°-60° C. The mixture is cooled and the tetrahydro-3,5-dioxo-1H-pyrrrolizine-7a(5H)-propanoic acid p-chlorobenzyl ester, saccharin sodium, and imitation cherry flavor are added. The volume is made up with Neobee M-5.

The invention is further illustrated by the following example of a Syrup for Reconstitution. The syrup can contain between 50 mg/5 ml and 500 mg/5 ml, depending on the amount of active that is utilized.

EXAMPLE 23

| Ingredient | Quantity |
|---|---|
| Tetrahydro-3,5-dioxo-1H—pyrrolizine-7a(5H)—propanoic acid p-chlorobenzyl ester | 10 g |
| Sugar granulated, Bottlers grade | 60 g |
| Artificial Peppermint Flavor, water Soluble | 0.4 g |
| Water q.s. ad | 100 ml |

The tetrahydro-3,5-dioxo-1H-pyrrolizine-7a(5H)-propanoic acid p-chlorobenzyl ester, granulated sugar, and artificial peppermint flavor are dry blended. The blend is filled into a bottle with a 100 ml calibration mark. At time of dispensing, make up to volume with water and shake until all solids are dissolved. The syrup contains 500 mg active per 5 ml. The mixture is refrigerated and used within seven days.

I claim:

1. A compound having the structural formula

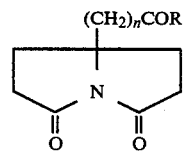

wherein n is zero to three, R is $NR_1R_2$ wherein $R_1$ is a 5- or 6-membered heterocyclic group selected from pyridinyl, tetrazol-5-yl, 1,2,3-triazol-5-yl, 1,2,4-triazol- 5-yl, 1,2-diazol-3-yl, 1,3-diazol-4-yl; 1,3,4-thiadiazol-2-yl, and 1,3,4-oxadiazol-2-yl which may be substituted by amino, alkylamino, or dialkylamino of from one to four carbon atoms; and $R_2$ is hydrogen or alkyl of from one to six carbon atoms.

2. A compound defined by claim 1 having the structural formula

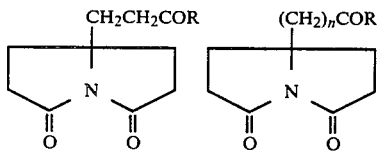

wherein R is $NR_1R_2$ wherein $R_2$ is hydrogen or alkyl of from one to six carbon atoms and $R_1$ is 4-amino-3-pyridinyl, 3-amino-4-pyridinyl, 4-pyridinyl, or 5-tetrazolyl.

3. The compound defined in claim 1 having the name of tetrahydro-3,5-dioxo-1H-pyrrolizine-7a(5H)-propanoic acid N-5-tetrazol-yl amide.

4. The compound defined in claim 1 having the name of tetrahydro-3,5-dioxo-1H-pyrrolizine -7a(5H)-propanoic acid N-4-pyridinyl amide.

5. A pharmaceutical composition for reversing amnesia caused by electroconvulsive shock comprising an effective amount of a compound having the structural formula

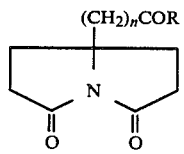

wherein n=0, 1, 2, 3, and $R_4$ is $NR_1R_2$ wherein $R_1$ is a 5- or 6-membered heterocyclic group selected from pyridinyl, tetrazol-5-yl, 1,2,3-triazol-5-yl, 1,2,4-triazol-5-yl, 1,2-diazol-3-yl, 1,3-diazol-4-yl; 1,3,4-thiadiazol-2-yl, and 1,3,4-oxadiazol-2-yl which may be substituted by amino, alkylamino, or dialkylamino of from one to four carbon atoms; and $R_2$ is hydrogen or alkyl of from one to six carbon atoms.

6. A method for reversing amnesia caused by electroconvulsive shock in a mammal in need of said treatment, which method comprises administering to said mammal the pharmaceutical composition defined in claim 5.

* * * * *